ns Patent [19]

Chu et al.

[11] Patent Number: 4,482,773
[45] Date of Patent: Nov. 13, 1984

[54] CATALYST FOR XYLENE ISOMERIZATION

[75] Inventors: Yung F. Chu, Cherry Hill, N.J.; Fritz A. Smith, Rye, N.Y.; Arthur W. Chester, Cherry Hill, N.J.

[73] Assignee: Mobil Oil Corporation, New York, N.Y.

[21] Appl. No.: 516,080

[22] Filed: Jul. 22, 1983

Related U.S. Application Data

[63] Continuation-in-part of Ser. No. 352,415, Feb. 25, 1982, abandoned.

[51] Int. Cl.³ ............................ C07C 5/24; C07C 5/30
[52] U.S. Cl. ...................................... 585/481; 502/62; 502/77; 585/482; 585/479; 585/488
[58] Field of Search ............... 585/481, 482, 483, 479, 585/486, 487, 488, 489, 28 M; 252/455 Z

[56] References Cited

U.S. PATENT DOCUMENTS

| | | | |
|---|---|---|---|
| 4,100,262 | 7/1978 | Pelrine | 502/77 |
| 4,159,282 | 6/1979 | Olson et al. | 585/481 |
| 4,163,028 | 7/1979 | Tabak et al. | 585/481 |
| 4,218,573 | 8/1980 | Tabak et al. | 502/77 |
| 4,236,996 | 12/1980 | Tabak et al. | 585/481 |

Primary Examiner—Delbert E. Gantz
Assistant Examiner—A. Pal
Attorney, Agent, or Firm—A. J. McKillop; M. G. Gilman; J. F. Powers, Jr.

[57] ABSTRACT

Isomerization of xylene in admixture with ethylbenzene by contact with a zeolite catalyst such as ZSM-5 is improved by use of a zeolite having a catalyst particle size of at least 1 micron and having incorporated thereon two metals such as platinum and magnesium.

7 Claims, 1 Drawing Figure

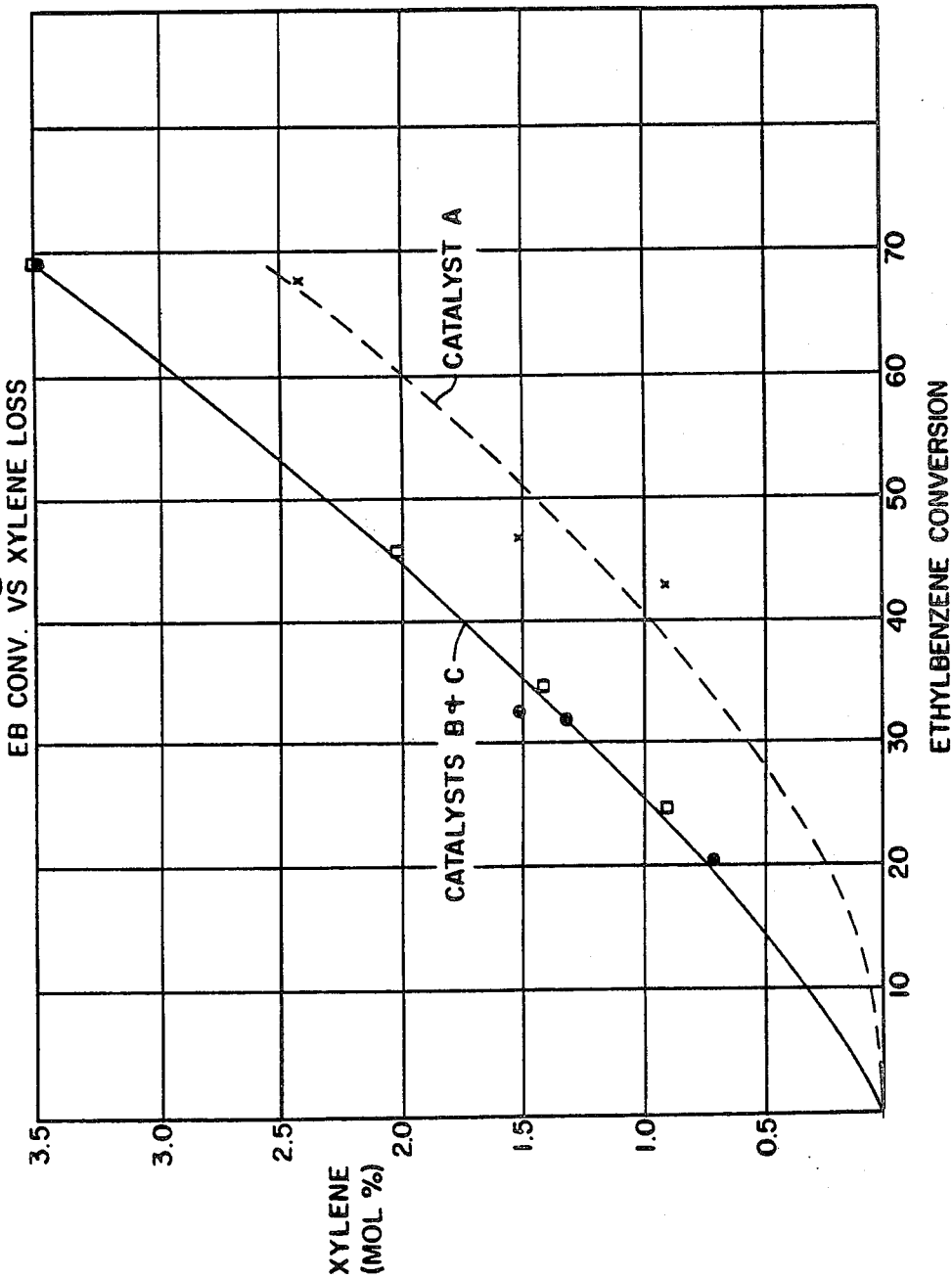

CATALYST FOR XYLENE ISOMERIZATION

This is a continuation-in-part application of U.S. Ser. No. 352,415, filed Feb. 25, 1982, now abandoned.

BACKGROUND OF THE INVENTION

1. Field of the Invention

This invention relates to a process for effecting isomerization of an aromatic $C_8$ mixture comprising ethylbenzene and xylene in the presence of a specified crystalline aluminosilicate zeolite catalyst characterized by a crystalline size of at least about 1 micron. The catalyst has associated with it platinum and a Group IIA metal. The invention also relates to a method of making a catalyst.

2. Description of the Prior Art

Xylene isomerization in the presence of a catalyst is well known to the art. U.S. Pat. No. 3,856,872 (Morrison) dated Dec. 24, 1974, shows a method of converting ethylbenzene over an active acid catalyst typified by zeolite ZSM-5. Ethylbenzene disproportionates to benzene and diethylbenzene which are readily separated from xylene by the distillation equipment needed in the loop to remove byproducts. It is recognized that rate of disproportionation of ethylbenzene is related to the rate of conversion of xylene into other compounds, e.g., by disproportionation. See also Burress, U.S. Pat. No. 3,856,873 which also describes reaction of $C_8$ aromatics over ZSM-5 and shows effects of various temperatures up to 950° F. in the absence of metal catalyst and in the absence of hydrogen. In the presence of the catalyst and operating at these higher temperatures, the transalkylation route for xylene losses is reduced; however, xylene losses via the disproportionation route is increased. The xylene loss byproducts are mostly trimethylbenzene, ethyl-xylene and $C_9+$ aromatics.

U.S. Pat. No. 4,098,837 (Chu) dated July 4, 1978, discloses a zeolite catalyst which incorporates phosphorus and one or more metals, including magnesium, in an effort to elicit a greater para-xylene content from the feed material. U.S. Pat. No. 4,159,282 (Olson et al) dated June 26, 1979, discloses xylene isomerization with a crystalline zeolite catalyst having a crystal size of at least 1 micron. The original alkaline metal of the zeolite may be replaced by ion exchange with suitable ions of Groups IB to VIII. A second metal, e.g., magnesium, may be combined with the zeolite.

U.S. Pat. No. 4,163,028 (Tabak et al) dated July 31, 1979, discloses xylene isomerization and ethylbenzene conversion at temperatures of 800° F. or higher with ZSM-5 or very high silica/alumina ratio whereby the acid activity is reduced.

U.S. Pat. No. 4,278,565 (Chen et al) dated July 14, 1981, discloses a zeolite catalyst having a crystalline size greater than 1 micron, e.g., HZSM-5C. Three metals are incorporated onto this catalyst: a Group IIB metal, a Group VIII metal and magnesium.

DESCRIPTION OF THE DRAWING

FIG. 1 shows a comparison of three isomerization processes.

SUMMARY OF THE INVENTION

It is possible to further reduce xylene byproduct formation by incorporating a second metal, e.g., platinum, into a Group IIA metal-containing catalyst having a crystalline size greater than 1 micron.

The process of the invention utilizes zeolite catalyst having a crystalline size of at least about 1 micron, usually in the approximate range of 1 to 20 microns and preferably 1 to 6 microns. The zeolite catalyst is essentially characterized by a silica to alumina ratio of at least about 12, a constraint index within the approximate range of 1 to 12, and by the fact that it contains both platinum and a metal from Group IIA, preferably magnesium.

The present process comprises isomerization of an aromatic $C_8$ mixture in the presence of the specified catalyst having a hydrogen to hydrocarbon ratio in the range of 0.1 to 10, and preferably 1 to 5, at a temperature between about 500° F. and 1000° F., preferably in excess of 650° F., at a pressure between 0 and about 1500 psig, utilizing a feed weight hourly space velocity (WHSV) between about 0.5 and about 50. The latter WHSV is based on the weight of catalyst composition, i.e., total weight of active catalyst and binder thereof.

DESCRIPTION OF SPECIFIC EMBODIMENTS

It is contemplated that any aromatic $C_8$ mixture containing ethylbenzene and xylene may be used as feed to the process of this invention. Generally, such mixture will have an ethylbenzene content in the approximate range of 5–50 wt. %, an ortho-xylene content in the approximate range of 0–15 wt. %, and a meta-xylene content in the approximate range of 0–70 wt. %. The feed may also contain nonaromatic hydrocarbons, i.e., naphthenes and paraffins. In a preferred embodiment, the invention provides means to process a mixture of $C_8$ aromatics to a mixture of reduced ethylbenzene content and increased content of para-xylene.

In accordance with the present invention, such feed is brought into contact, under conversion conditions, with a catalyst comprising a crystalline aluminosilicate zeolite having a crystal size of at least about 1 micron, a silica to alumina ratio of at least about 12 and a constraint index within the approximate range of 1 to 12. Such zeolites are well known to the art and suitable descriptions may be found in U.S. Pat. Nos. 4,159,282; 4,163,028; and 4,278,565, all of which are incorporated herein by reference. The preferred crystalline aluminosilicate zeolites are ZSM-5, ZSM-11, ZSM-12, ZSM-23, ZSM-35, and ZSM-38, with ZSM-5 particularly preferred.

The crystal size of the crystalline aluminosilicate zeolite employed in the process of the invention is at least about 1 micron, being in the approximate range of 1 to 20 microns and particularly in the range of 1 to 6 microns. The longer diffusional paths of zeolite crystals in excess of 1 micron further reduce byproduct formation thus decreasing xylene loss compared to zeolite crystals in the 0.5 micron range. Further, with the use of crystals within such size range distinctly higher selectivity for production of para-xylene has been observed as compared with comparable use of smaller size crystals.

The preferred catalyst will contain from about 0.5% to about 10%, preferably about 1% to about 5% by weight of the Group IIA component, e.g., magnesium, and about 0.01% to about 1%, preferably about 0.05% to about 1% by weight of platinum. The catalyst is prepared by conventional techniques including impregnation, base exchange, drying and air calcination. If desired the catalyst can be steamed for 1 or more hours at temperatures upwards of 300° F., the time pressure and temperature being inter-related such that less time is required at higher temperatures and/or pressures.

In the process of this invention, the feed is contacted with the above-described catalyst at a temperature between about 500° F. to about 950° F.; a contact time equivalent to or the same as a weight hourly space velocity (WHSV) of about 0.5 to about 50, preferably about 5 to about 25, and a pressure of about 0 to about 1500, preferably between about 20 and about 400 psig.

The reaction product effluent from the process of the invention contains ethane, benzene, toluene and other aromatic hydrocarbons with high selectivity for para-xylene. The combination of the larger size ZSM-5 crystal with two metals, e.g., platinum and magnesium, has been found to reduce the formation of byproducts, such as trimethylbenzene, ethyl-xylene, $C_9+$ aromatics, and increase benzene formation.

The following Examples will serve to illustrate the process of this invention without limiting the same.

CATALYST PREPARATION

HZSM-5 characterized by an average crystal size of about $2\mu$ was made conventionally using the tetrapropyl ammonium and sodium cations or tetramethyl ammonium and sodium cations.

The preferred catalyst is prepared by circulating a $Mg(NO_3)_2$ solution through a reactor bed containing HZSM-5 crystals until about 2.4% Mg is incorporated onto the catalyst. The catalyst is then dried at a temperature of about 250° F., and air calcined at 1000° F. for 3 hours. This procedure is followed by impregnation of 0.1% Pt on the catalysts which is further dried and air calcined at a temperature of 1000° F. for an additional 3 hours. This catalyst will hereinafter be referred to as Catalyst A.

Examples 1-3

A feed constituting a blend of ethylbenzene and mixed xylenes, having a composition set forth in Table 1 below, was tested in three different pressurized xylene isomerization units. In Example 1, the feed was passed over a catalyst comprising a platinum impregnated HZSM-5 (no magnesium) characterized by an average crystal size of 0.1 microns, hereinafter referred to as Catalyst B, at a temperature of 853° F., a pressure of 100 psig and WHSV of 14.7. In Example 2, the feed was passed over a catalyst comprising a platinum impregnated HZSM-5 (no magnesium) characterized by an average crystal size of 0.1 microns hereinafter referred to as Catalyst C, at a temperature of 677° F., a pressure of 100 psig and a WHSV of 7.0. In Example 3, the feed was passed over Catalyst A at a temperature of 700° F., a pressure of 100 psig and a WHSV of 6.5. The product compositions and selectivities obtained in each instance are given in Table 1.

In this and other tables hereinafter set forth:
Xylene loss (mole %) is calculated by:

$$\text{Xylene loss} = \frac{[T]_{P-F} + [TMB]_{P-F} + [EX]_{P-F}}{[P - X + M - X + O - X]_F} \times 100$$

P=product; F=feed; [ ]=mole %
$H_2/HC$ Molar Ratio is the molar ratio of $H_2$ and hydrocarbons in the feed.
EB Conv. wt. % is the weight percent conversion of ethylbenzene.

P-Xylene Equil. Approach % is the weight percent equilibrium approach of p-xylene.

$C_2=/C_2$ is the molar ratio of ethylene and ethane in the product.

$\Delta EB$ is the amount of ethylbenzene converted.

BZ is the amount (moles) of benzene formed in the product.

$C_2/\Delta EB$ is the molar ratio of ethane produced per mole of ethylbenzene converted.

$BZ/\Delta EB$ is the molar ratio of benzene produced per mole of ethylbenzene converted.

$C_1-C_4$ ($C_5-C_9$) N. A. is the $C_1-C_4$ and $C_5-C_9$ nonaromatics formed in the product.

TABLE 1

| Example No. | 1 | | 2 | | 3 | |
|---|---|---|---|---|---|---|
| Catalyst | B | | C | | A | |
| Temperature °F. | 853 | | 677 | | 700 | |
| Pressure, psig | 100 | | 100 | | 100 | |
| WHSV | 14.7 | | 7.0 | | 6.5 | |
| $H_2/HC$ Molar Ratio | 2.2 | | 2.0 | | 2.0 | |
| Product Analysis (wt. %) | Feed | | Feed | | Feed | |
| $C_1-C_4$ N. A. | | 0.7 | | 0.7 | | 1.4 |
| $C_5-C_9$ N. A. | | 0.0 | | 0.1 | | 0.7 |
| BZ | | 2.2 | | 1.6 | | 2.5 |
| Toluene | 1.5 | 2.1 | 1.5 | 2.1 | 1.5 | 1.9 |
| Ethylbenzene | 8.1 | 5.2 | 8.6 | 5.7 | 9.0 | 5.1 |
| P—Xylene | 9.2 | 21.3 | 9.4 | 21.5 | 8.8 | 21.4 |
| M—Xylene | 61.3 | 46.8 | 60.8 | 47.1 | 61.4 | 47.8 |
| O—Xylene | 19.9 | 20.7 | 19.7 | 19.9 | 19.3 | 18.6 |
| Ethyltoluene | | 0.1 | | 0.3 | | 0.2 |
| Trimethylbenzene | | 0.7 | | 0.5 | | 0.3 |
| Diethylbenzene | | >0 | | 0.2 | | 0.2 |
| Ethyl-Xylene | | 0.1 | | 0.3 | | >0 |
| $C_{10}$ | | — | | — | | — |
| EB Conv. wt. % | | 35 | | 33 | | 43 |
| Xylene Loss, Mole % | | 1.4 | | 1.5 | | 0.9 |
| P—Xylene Equil. Approach % | | 105 | | 105 | | 105 |
| $C_2=/C_2$ | | 0 | | 0 | | 0 |
| $C_2/\Delta EB$ | | 0.8 | | 0.5 | | 0.9 |
| $BZ/\Delta EB$ | | 1.1 | | 0.8 | | 0.9 |

A comparison of the xylene selectivities of the three isomerization processes utilized in the above example is shown in FIG. 1. Referring more particularly to this FIGURE, selectivity is expressed in terms of the ratio of xylene loss to relative ethylbenzene conversion. It will be evident that there is a marked improvement in selectivity obtained utilizing Catalyst A over conventional use of conventional catalysts exemplified by Catalysts B and C. At about 50% ethylbenzene conversion, the xylene loss advantage for the improved Catalyst A is about 0.9% per pass.

What is claimed is:

1. A process for isomerizing an isomerization feed containing an aromatic $C_8$ mixture of ethylbenzene and xylene in which the para-xylene content is less than equilibrium which comprises contacting said feed, under conversion conditions with a catalyst comprising crystalline aluminosilicate zeolite ZSM-5 predominantly in the hydrogen form and having a crystal size of at least about 1 micron, said zeolite containing platinum and a Group IIA component.

2. The process of claim 1 wherein said conversion conditions include a temperature of from about 500° F. to about 1000° F., a pressure of about 0 to about 1500 psig and a weight hourly space velocity of between about 0.5 and about 100.

3. The process of claim 1 wherein said aromatic $C_8$ mixture consists essentially of ethylbenzene, para-xylene, meta-xylene and ortho-xylene.

4. The process of claim 1 wherein the Group IIA metal is magnesium.

5. The process of claim 1 wherein said crystalline aluminosilicate zeolite HZSM-5 is characterized by an average crystal size of about 2 microns.

6. The process of claim 1 wherein the crystal size of said crystalline aluminosilicate zeolite is within the approximate range of 1 to 20 microns.

7. The process of claim 1 wherein the crystal size of said crystalline aluminosilicate zeolite is within the approximate range of 1 to 6 microns.

* * * * *